United States Patent
Pineau et al.

(10) Patent No.: US 9,188,582 B2
(45) Date of Patent: Nov. 17, 2015

(54) METHOD FOR PREDICTING THE PRESENCE OF REPRODUCTIVE CELLS IN TESTIS

(71) Applicants: INSERM (INSTITUT NATIONAL DE LA SANTE ET DE LA RECHERCHE MEDICALE), Paris (FR); UNIVERSITE DE RENNES 1, Rennes (FR)

(72) Inventors: Charles Pineau, Rennes (FR); Antoine Rolland, Rennes (FR); Pierre Calvel, Rennes (FR); Regis Lavigne, Rennes (FR)

(73) Assignees: INSERM (Institut National de la Santé et de la Recherche Médicale), Paris (FR); Université de Rennes 1, Rennes (FR); Université des Antilles et de la Guyane, Pointe-à-Pitre (FR)

( * ) Notice: Subject to any disclaimer, the term of this patent is extended or adjusted under 35 U.S.C. 154(b) by 0 days.

(21) Appl. No.: 14/355,227

(22) PCT Filed: Oct. 31, 2012

(86) PCT No.: PCT/EP2012/071598
§ 371 (c)(1),
(2) Date: Apr. 30, 2014

(87) PCT Pub. No.: WO2013/064555
PCT Pub. Date: May 10, 2013

(65) Prior Publication Data
US 2014/0302522 A1      Oct. 9, 2014

(30) Foreign Application Priority Data

Nov. 2, 2011   (EP) .................................. 11306409

(51) Int. Cl.
*G01N 33/48*    (2006.01)
*G01N 33/50*    (2006.01)
*G01N 33/68*    (2006.01)

(52) U.S. Cl.
CPC .......... *G01N 33/5091* (2013.01); *G01N 33/689* (2013.01); *G01N 2800/367* (2013.01)

(58) Field of Classification Search
None
See application file for complete search history.

(56) References Cited

U.S. PATENT DOCUMENTS

2006/0199204 A1   9/2006   Dix et al.
2013/0210666 A1*  8/2013   Jarvi et al. ................. 506/9

OTHER PUBLICATIONS

Kumar et al., Proteomic analysis of heparin-binding proteins from human seminal plasma: a step towards identification of molecular marker of male infertility, J. Biosci. 34(6), Dec. 2009, pp. 899-908.*
Wang et al., "Proteomic analysis of seminal plasma from asthenozoospermia patients reveals proteins that affect oxidative stress responses and semen quality", Asian Journal of Andrology, May 18, 2009, pp. 484-491, vol. 11, No. 4.
Starita-Geribaldi et al., "Mapping of seminal plasma proteins by two-dimensional gel electrophoresis in men with normal and impaired spermatogenesis", Molecular Human Reproduction, Aug. 2001, pp. 715-722, vol. 7, No. 8.
Pilch et al., "Large-scale and high-confidence proteomic analysis of human seminal plasma", Genome Biology, May 18, 2006, p. R40, vol. 7, No. 5, Biomed Central Ltd., London, GB.

* cited by examiner

*Primary Examiner* — Gary W Counts
(74) *Attorney, Agent, or Firm* — Whitham, Curtis, Christofferson & Cook, P.C.

(57) ABSTRACT

Testicular germline markers and their use for predicting the presence or not of reproductive cells in testis of an infertile or hypo fertile male subject are provided. More particularly, identification of specific protein biomarkers of post-meiotic germ cells in the human seminal plasma was carried out by an integrative genomics approach. It was demonstrated that the presence of such biomarkers could be monitored in the seminal plasma of azoospermic subjects in order to select for a testis biopsy and testicular sperm extraction (TESE) only subjects for which there are high probabilities to find reproductive cells. The results indicate the analysis of seminal plasma is a non-invasive approach for predicting the presence of reproductive cells.

7 Claims, 1 Drawing Sheet

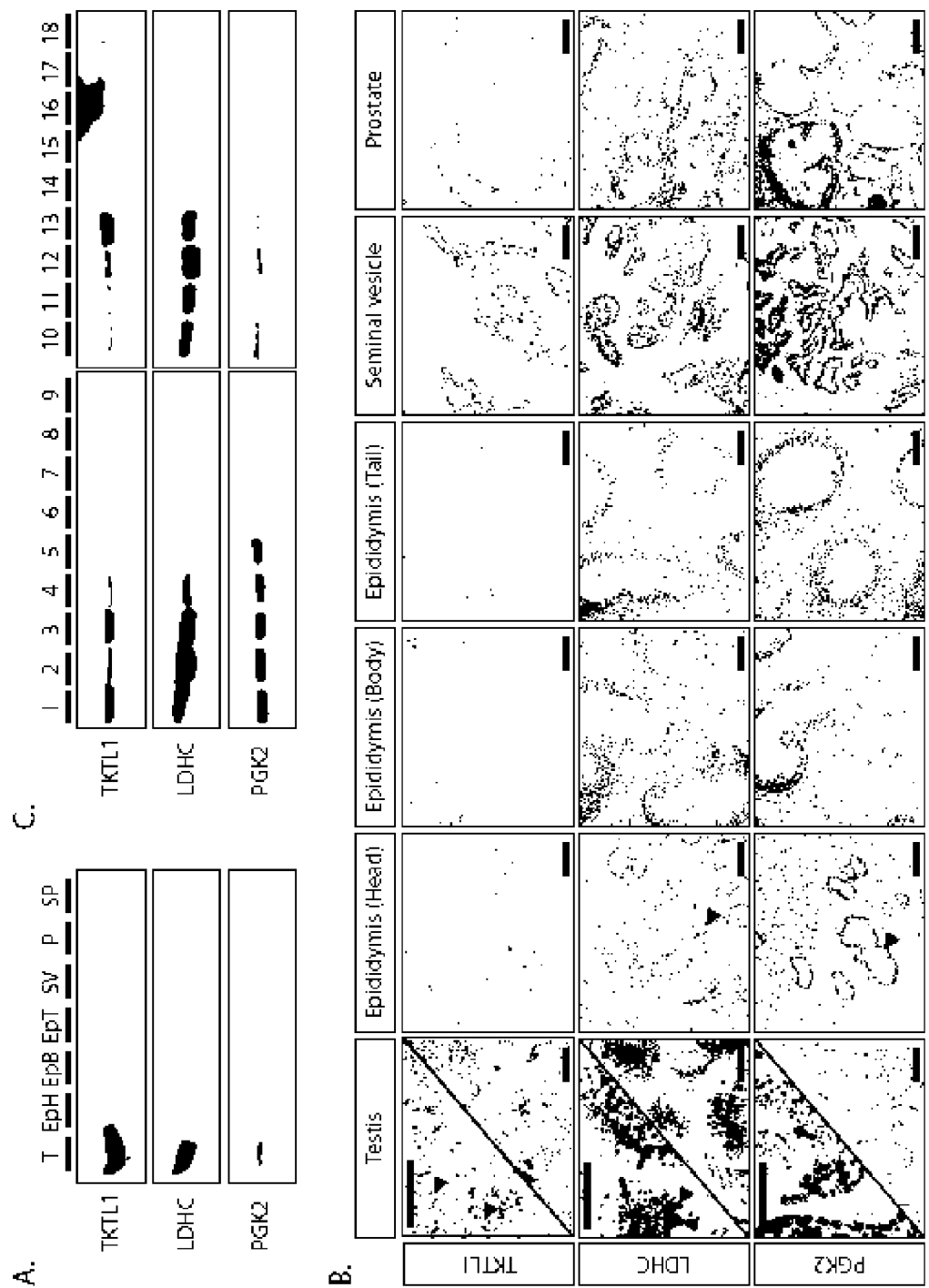

METHOD FOR PREDICTING THE PRESENCE OF REPRODUCTIVE CELLS IN TESTIS

FIELD OF THE INVENTION

The present invention relates to testicular germline markers and their use for predicting the presence or not of reproductive cells in testis of an infertile or hypofertile male subject.

BACKGROUND OF THE INVENTION

Infertility is a common problem throughout the world. Approximately fifteen percent of all couples encounter fertility problems during their reproductive lifetime and in about half of the cases the cause is of male origin (1-2). Despite the possible deleterious role of lifestyle, environmental and/or genetic factors evoked on male reproduction, the aetiologies of most infertility cases remain unknown. According to various sources, male factors represent about one third to 40% of all infertility situations. Routine semen analysis may indicate defective sperm production or diminished sperm motility as well as an abnormal sperm morphology resulting of a defective spermiogenesis. It may also reveal the absence of spermatozoa in semen, a situation termed azoospermia which concerns about 8% of men with fertility problems (3). It is the consequence of either an obstructed or discontinuous male genital tract such as the bilateral agenesis of the vas deferens (obstructive azoospermia; OA) or a failure of the testis to initiate or maintain spermatogenesis due to endogenous or exogenous abnormalities (non-obstructive azoospermia, NOA).

One of the most dramatic revolutions to occur in the field of assisted reproductive technology over the past two decades was the introduction of intracytoplasmic sperm injection (ICSI), which has indeed revolutionized the treatment of severe male infertility (4). For men with azoospermia, surgical retrieval of sperm cells from the epididymis or testicular biopsies in combination with ICSI opened new avenues in the management of male infertilities (5-7). In the vast majority of obstructive cases, spermatozoa are often abundant in the epididymis or seminiferous tubules, thus allowing high rates of retrieval through percutaneous epididymal sperm aspiration (PESA), microepididymal sperm aspiration (MESA) or testicular sperm aspiration (TESA) (8). However, in NOA subjects, the epididymis is devoid of spermatozoa and spermatogenesis is severely impacted or reduced. Regardless of the underlying aetiology, which often remains unexplained, restoring the fertility of NOA subjects generally relies on recovering spermatozoa from testicular biopsies via a sperm extraction procedure (testicular sperm extraction; TESE), which is then followed by in vitro fertilization with ICSI (9). Unfortunately, testicular spermatozoa are found in only around 50% to markedly lower rates of subjects with NOA (10). This poor result is due to the fact that both testes may be devoid of germ cells (i.e. Sertoli-Cell-Only syndrome; SCO), house an incomplete spermatogenesis (i.e. maturation arrest) or, under the best circumstance, contain only scarce residual sites of complete spermatogenesis. In the latter situation, spermatozoa can be retrieved by chance from a testis biopsy. This is the reason why counseling is crucial in the management of infertile men. None of the subjects parameters examined to date have been shown to predict successful biopsy/TESE outcomes (11).

Thus, it appears crucial for clinicians to identify factors that may predict a high probability of spermatozoa retrieval since unsuccessful sperm recovery procedures have significant emotional and financial implications. However, none of the examined parameters to date could be used to predict successful outcomes (11).

Apart from its obvious role in transporting male gametes, the seminal plasma provides a protective environment for ejaculated spermatozoa and improves their fertilization potential. Seminal plasma is a highly complex fluid, which contains proteins secreted from several glands in the male reproductive tract, including the testis, epididymis, seminal vesicles and prostate. Indeed, like most body fluids, seminal plasma contains many proteins at widely different concentrations, which renders scarce proteins very difficult to identify and quantify. Also, reproductive disorders can cause certain compositional changes that are known to alter the properties of seminal plasma. Thus, this bio fluid is considered to be a promising source of biomarkers of male infertility and/or pathologies of the male genital tract. In addition, although its production may be altered, seminal plasma continues to be produced in most cases of infertility. Over the past decade, several studies have investigated the protein composition of seminal plasma in healthy donors and have identified numerous proteins through proteomic analyses (12). For example, a large-scale mass spectrometric analysis of human seminal plasma, conducted using an LTQ-FTICR instrument, allowed 923 seminal plasma proteins to be identified with high confidence (13). However, most previous studies have failed to identify known components of the seminal plasma, such as human beta-defensins (e.g., HBD1). This confirms that accessing the proteins present at very low concentrations is hampered by the overwhelming signals produced by a few dominant proteins. Indeed, thorough analysis of very complex biofluids requires an optimized strategy that is not exclusively based on mass spectrometry sensitivity and dynamic range.

However, there is a need to identify non-invasive technique and new methods for predicting the presence of reproductive cells in testis of an infertile or hypofertile subjects. In this way, it has been suggested that the characterization of new testicular germline biomarkers in the seminal plasma may be highly desirable.

SUMMARY OF THE INVENTION

The present invention relates to a method for predicting the presence of reproductive cells in the testis of an infertile or hypofertile male subject, comprising a step of detecting in a seminal plasma sample obtained from said subject at least one biomarker selected from Tables 1, 2, 3, 4, or 5 wherein said biomarkers are CELSR1, CT47A1-9, ART3, MAPK1, ARHGAP9, PTPN21, ZNF569, TFRC, TMED4, MLLT4, MKI67, HIST1H2BJ, DSG1, FGG, HIST1H2BA, GART, MCM3AP, PITHD1, AMBP, SI, SLC44A5, GNAO1, GNAS, ANXA2, INPP4B, SLC7A2, APOA2, EEF1E1, MAP6, RAB27B, ABCB11, SEMA3D, ATP1B3, DNASE1, TOLLIP, BROX, AHCYL2, PSMD6, TPPP2, PRDD54, AQP5, PRKACG, XPNPEP1, GALC, FAM35B, ACE, DDX3X, EIF4A2, PRND, PGLYRP2, TUBB4, INHA, ACE2, APOA1, ZDHHC20, TEX101, DPEP3, PRPS1L1, ZPBP, ZPBP2, ADAM32, TEKT3, GAPDHS, TRIM36, TKTL2, SPAM1, LYZL2, SPACA3, OTUB2, AKAP4, RFFL, GLYPR1L1, TKTL1, LDHC, PGK2, AHSG and PGAM2.

DETAILED DESCRIPTION OF THE INVENTION

The inventors have carried out an identification of specific protein biomarkers of post-meiotic germ cells in the human seminal plasma by an integrative genomics approach named "combinatorial Omics". They demonstrated that the presence of such biomarkers could be monitored in the seminal plasma of azoospermic subjects in order to select for a testis biopsy and TESE only subjects for which there are high probabilities to find reproductive cells. Their results indicate the analysis of seminal plasma is a non-invasive approach for predicting the presence of reproductive cells.

More particularly, the inventors have performed a proteomic characterization of human seminal plasma using combinatorial peptide ligand library technology, which is now considered to be an efficient approach to minimizing the dynamic range of protein concentrations in complex mixtures (14-17). This method is based on treating the sample with a highly diversified hexapeptide ligand library immobilized on solid phase matrix. In theory, such a library condenses the dynamic range of the protein concentrations while retaining a large proportion of the entire protein repertoire present in the initial sample. This strategy has been used to efficiently prefractionate biofluids such as urine (18), serum (19) and cerebrospinal fluid (CSF) (20), and to extensively characterize the proteomes of isolated populations of platelets (21) and red blood cells (22).

To identify the low-copy-number proteins present in the seminal plasma proteome, the inventors combined several techniques and strategies. The inventors prefractionated human seminal plasma from a healthy donor and then subjected it to an extensive protein identification method designed for complex samples, which involved iterative nano-LC-MS/MS analysis, exclusion list generation and iterative database searching with Proteome Discoverer™ software. The set of proteins identified was compared, merged and supplemented with existing human seminal plasma protein datasets, leading to a list of more than 1,000 unique proteins. The inventors developed a "combinatorial omics" approach based on an intuitive mining of the protein dataset using Affymetrix microarray tissue-profiling expression data, which allowed potentially relevant functional biomarkers to be identified for the testis participating in seminal plasma production. For a small subset of the identified germ cell-specific proteins, immunoblot analysis of normal and pathological seminal plasma samples (e.g., OA, NOA and post-vasectomy), together with immunohistochemistry experiments, validated our candidate selection strategy.

Accordingly, the present invention relates to a method for predicting the presence of reproductive cells in the testis of an infertile or hypofertile male subject, comprising a step of detecting in a seminal plasma sample obtained from said subject at least one biomarker selected from Tables 1, 2, 3, or 4.

Typically, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 biomarkers may be selected from tables 1, 2, 3 and 4.

As used herein, the term "subject" denotes a mammal, such as a rodent, a bovine, an ovine, a feline, a canine, and a primate. Preferably a subject according to the invention is a human.

In a preferred embodiment of the invention, a subject refers to any subject (preferably human) afflicted with male infertility due to azoospermia. In a particular embodiment, the subject is afflicted with non-obstructive azoospermia.

As used herein the term "reproductive cells" refers to a male gamete or male germ cells that after fertilization produce embryo leading to pregnancy. The term "reproductive cells" as used herein preferably means post-meiotic germ cells capable of fertilizing the oocyte and passing along its genetic information to the next generation. In one embodiment, the reproductive cells are spermatids, preferably late spermatids, more preferably spermatozoa.

All the biomarkers pertaining to the invention are known per se, and are listed in the below Tables 1, 2, 3, 4 and 5. Tables 1, 2, 3, 4 and 5 present the set of testicular germline biomarkers whose combined expression profile has been shown to be informative for selecting for a testis biopsy only subjects for which there are high probabilities to find reproductive cells.

In one embodiment, the biomarkers of the invention include amino acid sequences that are substantially identical to biomarkers of Tables 1, 2, 3, 4 and 5 and having at least about 80% sequence identity, more preferably 85% sequence identity, and even more preferably 90-95% sequence identity to biomarkers of Tables 1, 2, 3, 4 and 5.

TABLE 1 set of predictive testis reproductive cells biomarkers

| Gene name | Polypeptide name | Polypeptide ID |
| --- | --- | --- |
| CELSR1 | Cadherin EGF LAG seven-pass G-type receptor 1 | Q9NYQ6 |
| CT47A1-9 | Cancer/testis antigen 47A | Q5JQC4 |
| ART3 | Ecto-ADP-ribosyltransferase 3 | Q13508 |
| MAPK1 | Mitogen-activated protein kinase 1 | P28482 |
| ARHGAP9 | Rho GTPase-activating protein 9 | Q9BRR9 |
| PTPN21 | Tyrosine-protein phosphatase non-receptor type 21 | Q16825 |
| ZNF569 | Zinc finger protein 569 | Q5MCW4 |
| TFRC | Transferrin receptor protein 1 | P02786 |
| TMED4 | Transmembrane emp24 domain-containing protein 4 | Q7Z7H5 |
| MLLT4 | Afadin | P55196 |
| MKI67 | Antigen KI-67 | P46013 |
| HIST1H2BJ | Histone H2B type 1-J | P06899 |
| DSG1 | Desmoglein-1 | Q02413 |
| FGG | Fibrinogen gamma chain | P02679 |
| HIST1H2BA | Histone H2B type 1-A | Q96A08 |
| GART | Trifunctional purine biosynthetic protein adenosine-3 | P22102 |
| MCM3AP | 80 kDa MCM3-associated protein | O60318 |
| PITHD1 | PITH domain-containing protein 1 | Q9GZP4 |
| AMBP | Protein AMBP | P02760 |
| SI | Sucrase-isomaltase, intestinal | P14410 |
| SLC44A5 | Choline transporter-like protein 5 | Q8NCS7 |
| GNAO1 | Guanine nucleotide-binding protein G(o) subunit alpha | P09471 |

TABLE 1-continued set of predictive testis reproductive cells biomarkers

| Gene name | Polypeptide name | Polypeptide ID |
|---|---|---|
| GNAS | Guanine nucleotide-binding protein G(s) subunit alpha isoforms short | P63092 |
| ANXA2 | Annexin A2 | P07355 |
| INPP4B | Type II inositol-3,4-bisphosphate 4-phosphatase | O15327 |
| SLC7A2 | Low affinity cationic amino acid transporter 2 | P52569 |
| APOA2 | Apolipoprotein A-II | P02652 |
| EEF1E1 | Eukaryotic translation elongation factor 1 epsilon-1 | O43324 |
| MAP6 | Microtubule-associated protein 6 | Q96JE9 |
| RAB27B | Ras-related protein Rab-27B | O00194 |
| ABCB11 | Bile salt export pump | O95342 |
| SEMA3D | Semaphorin-3D | O95025 |
| ATP1B3 | Sodium/potassium-transporting ATPase subunit beta-3 | P54709 |
| DNASE1 | Deoxyribonuclease-1 | P24855 |
| TOLLIP | Toll-interacting protein | Q9H0E2 |
| BROX | BRO1 domain-containing protein BROX | Q5VW32 |
| AHCYL2 | Putative adenosylhomocysteinase 3 | Q96HN2 |
| PSMD6 | 26S proteasome non-ATPase regulatory subunit 6 | Q15008 |
| TPPP2 | Tubulin polymerization-promoting protein family member 2 | P59282 |
| PRDD54 | Inactive serine protease 54 | Q6PEW0 |
| AQP5 | Aquaporin-5 | P55064 |
| PRKACG | cAMP-dependent protein kinase catalytic subunit gamma | P22612 |
| XPNPEP1 | Xaa-Pro aminopeptidase 1 | Q9NQW7 |
| GALC | Galactocerebrosidase | P54803 |
| FAM35B | Protein FAM35B | Q49AJ0 |
| ACE | Angiotensin-converting enzyme | P12821 |
| DDX3X | ATP-dependent RNA helicase DDX3X | O00571 |
| EIF4A2 | Eukaryotic initiation factor 4A-II | Q14240 |
| PRND | Prion-like protein doppel | Q9UKY0 |
| PGLYRP2 | N-acetylmuramoyl-L-alanine amidase | Q96PD5 |
| TUBB4 | Tubulin beta-4 chain | P04350 |
| INHA | Inhibin alpha chain | P05111 |
| ACE2 | Angiotensin-converting enzyme 2 | Q9BYF1 |
| APOA1 | Apolipoprotein A-I | P02647 |

TABLE 2 set of predictive spermatogonia/germline biomarkers

| Polypeptide Symbol | Polypeptide name | Polypeptide ID |
|---|---|---|
| ZDHHC20 | Probable palmitoyltransferase ZDHHC20 | Q5W0Z9 |
| TEX101 | Testis-expressed protein 101 | Q9BY14 |
| DPEP3 | Dipeptidase 3 | Q9H4B8 |

TABLE 3 set of predictive spermatocytes/spermatids biomarkers

| Polypeptide Symbol | Polypeptide name | Polypeptide ID |
|---|---|---|
| PRPS1L1 | Ribose-phosphate pyrophosphokinase 3 | P21108 |
| ZPBP | Zona pellucida-binding protein 1 | Q9BS86 |
| ZPBP2 | Zona pellucida-binding protein 2 | Q6X784 |
| ADAM32 | Disintegrin and metalloproteinase domain-containing protein 32 | Q8TC27 |
| TEKT3 | Tektin-3 | Q9BXF9 |
| GAPDHS | Glyceraldehyde-3-phosphate dehydrogenase, testis-specific | O14556 |
| TRIM36 | E3 ubiquitin-protein ligase TRIM36 | Q9NQ86 |
| TKTL2 | Transketolase-like protein 2 | Q9H0I9 |

TABLE 4 set of predictive spermatids biomarkers

| Polypeptide Symbol | Polypeptide name | Polypeptide ID |
|---|---|---|
| SPAM1 | Hyaluronidase PH-20 | P38567 |
| LYZL2 | Lysozyme-like protein 2 | Q7Z4W2 |
| SPACA3 | Sperm acrosome membrane-associated protein 3 | Q8IXA5 |
| OTUB2 | Ubiquitin thioesterase OTUB2 | Q96DC9 |
| AKAP4 | A-kinase anchor protein 4 | Q5JQC9 |
| RFFL | E3 ubiquitin-protein ligase rififylin | Q8WZ73 |
| GLYPR1L1 | GLIPR1-like protein 1 | Q6UWM5 |

TABLE 5 set of predictive testis reproductive cells biomarkers already disclosed in the prior art

| Polypeptide Symbol | Polypeptide name | Polypeptide ID |
|---|---|---|
| TKTL1 | Transketolase-like protein 1 | P51854 |
| LDHC | L-lactate dehydrogenase C chain | P07864 |
| PGK2 | Phosphoglycerate kinase 2 | P07205 |
| AHSG | Alpha-2-HS-glycoprotein | P02765 |
| PGAM2 | Phosphoglycerate mutase 2 | P15259 |

As used herein the term "detecting" refers to detecting the presence of the biomarkers or proteins of the invention. The term "detecting" as used herein also includes measuring the expression level of the biomarkers of the invention.

In one embodiment, the method may further comprise a step of detecting in the seminal plasma sample of said subject at least one biomarker of table 5. In one embodiment 1, 2, 3, 4 or 5 biomarkers may be selected from Table 5.

In one embodiment the method comprises a step of detecting in a seminal plasma sample of said subject 77 biomarkers wherein said biomarkers are CELSR1, CT47A1-9, ART3, MAPK1, ARHGAP9, PTPN21, ZNF569, TFRC, TMED4, MLLT4, MKI67, HIST1H2BJ, DSG1, FGG, HIST1H2BA, GART, MCM3AP, PITHD1, AMBP, SI, SLC44A5, GNAO1, GNAS, ANXA2, INPP4B, SLC7A2, APOA2, EEF1E1, MAP6, RAB27B, ABCB11, SEMA3D, ATP1B3, DNASE1, TOLLIP, BROX, AHCYL2, PSMD6, TPPP2, PRDD54, AQP5, PRKACG, XPNPEP1, GALC, FAM35B, ACE, DDX3X, EIF4A2, PRND, PGLYRP2, TUBB4, INHA, ACE2, APOA1, ZDHHC20, TEX101, DPEP3, PRPS1L1, ZPBP, ZPBP2, ADAM32, TEKT3, GAPDHS, TRIM36, TKTL2, SPAM1, LYZL2, SPACA3, OTUB2, AKAP4, RFFL, GLYPR1L1, TKTL1, LDHC, PGK2, AHSG, PGAM2.

Detecting the biomarkers as above described in Table 1, 2, 3, 4 and 5 can be performed by a variety of techniques.

Typically, the detection comprises contacting the sample with a binding partner directed against said biomarker, and thereby detecting the presence, or measuring the amount, of said biomarker in the seminal sample. As used herein, the term "binding partner" refers to any molecule (natural or not) that is able to bind the biomarker with high affinity. Said binding partners include but are not limited to antibodies, aptamers, and peptides. Contacting may be performed in any suitable device, such as a plate, microtiter dish, test tube, well, glass, column, and so forth. In specific embodiments, the contacting is performed on a substrate coated with the binding partner. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as an antibody-antigen complex, to be formed between the binding partner and the biomarker of the sample.

In a preferred embodiment, methods for detecting said biomarkers also include the determination of the level of said biomarkers.

The presence of the biomarker can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; glass slides, activated beads, magnetically responsive beads, and the like.

More particularly, an ELISA method can be used, wherein the wells of a microtiter plate are coated with an antibody against the protein to be tested. A biological sample containing or suspected of containing the marker protein is then added to the coated wells. After a period of incubation sufficient to allow the formation of antibody-antigen complexes, the plate (s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

The presence of the biomarker of the invention can also be detected using mass spectrometry, more particularly, a SRM/MRM (Selected Reaction Monitoring/Multiple Reaction Monitoring) mass spectrometry technique (54).

The methods of the invention may further comprise a step consisting of comparing the expression level of the biomarkers detected in the seminal plasma sample with a reference value, wherein detecting differential in the expression of the biomarkers between the sample and the reference value is indicative of the probability to find reproductive cells in the testis of the subject.

Typically, the reference value may correspond to the expression level determined for one biomarker of the invention in the seminal plasma sample of a fertile subject. Accordingly higher or equal biomarkers expression level in the seminal plasma sample than reference value is indicative for a high probability to find reproductive cells in the testis of the subject.

Alternatively, the reference value may correspond to the expression level for one biomarker of the invention in the seminal plasma sample of an infertile subject. Accordingly, a higher expression level in the seminal plasma sample than the reference value is indicative of a high probability to find reproductive cells in the testis of the subject and lower or equal biomarkers expression level in the seminal plasma sample than reference value is indicative for a low probability to find reproductive cells in the testis of the subject.

In some embodiments, the method of the invention may include calculating a score for predicting the presence of reproductive cells in a testis of an infertile or hypofertile male subject, which is derived from running a model that include the predicting factor determined for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 or 77 biomarkers of the invention. For calculating the score, the predicting factor determined for a single biomarker of the invention may be pondered by a coefficient. The weight given to each biomarker is based on its contribution relative to the other biomarkers in the prediction of the presence of reproductive cells in the testis of the infertile or hypofertile male subject. Typically, the method for calculating the score is based on statistical studies performed on various cohorts of subjects. The score may also include other various subject parameters (e.g., age, weight, race, levels of circulating FSH, microdeletion of Y chromosome, diabetes, cryptorchidia antecedents). In some embodiments, a computer program may thus generate the probability score.

The method of the invention is particularly suitable for determining whether a procedure for recovering reproductive cells in the testis of the infertile or hypofertile male subject shall be performed with a reasonable expectation of success. In case when there is a high probability to find reproductive cells in the testis of the subject, a procedure for recovering reproductive cells may be performed via a biopsy.

If the embryologist is able to find reproductive cells that are capable of fertilizing the oocyte then he can proceed with classical in vitro fertilization (cIVF) or to intracytoplasmic sperm injection (ICSI) protocol. The term "classical in vitro fertilization" or "cIVF" refers to a process by which oocytes are fertilized by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization, especially that associated with sperm donation.

Typically when the embryologist detect in the seminal plasma sample of the subject at least one biomarker, preferably 2, 3, 4, 5, 6 or 7 biomarkers of Table 4, there is a high probability to find spermatids in a testis of the subject. Then the embryologist may perform a testis biopsy and can try to isolate spermatids from said biopsy. If spermatids can be recovered, the embryologist can perform the intracytoplasmic injection of the nucleus of a spermatid into an oocyte.

If the embryologist is not able to find reproductive cells that are capable of fertilizing the oocyte, but is able to find germ cells, then he can performed in vitro spermatogenesis by any method known in the art (52-53). Then after such a method, the embryologist may use the obtained spermatozoids for proceeding to classical in vitro fertilization (cIVF) or to intracytoplasmic sperm injection (ICSI) protocol.

The method of the invention is also particularly suitable for monitoring a treatment capable of restoring normal spermatogenesis. Typically, said treatment may be an azoospermia treatment. The "azoospermia treatment" relate to any type of azoospermia therapy undergone by the azoospermic subjects previously to collecting the azoospermic seminal plasma samples, including gonadotropin, Human Chorionic Gonadotropin (HCG), Human Menopausal Gonadotropin (HMG), bromocryptine and surgery, e.g. vasoepididymal anastomosis (VEA), vasovasal anastomosis (VVA) and Microsurgical Vasovasostomy (Micro VVA).

The method of the invention can be applied for monitoring the sterilization treatment (e.g., drug compounds) of a male subject. For example, the effectiveness of an agent to affect the biomarkers expression (as herein after described) according to the invention can be monitored during treatments of subjects receiving sterilization treatments. The "sterilization treatment" relate to any type of sterilization therapy undergone by the male subjects, including vasectomy, non-hormonal sterilization, hormonal sterilization.

The invention also relates to a kit for performing the methods as above described, accordingly, the present invention relates to a kit for predicting the presence of reproductive cells in a testis of an infertile or hypofertile male subject, comprising means for detecting in a seminal plasma sample obtained from said subject at least one, preferably at least two biomarkers selected from the Tables 1, 2, 3, 4. Typically, the kit may comprise means for detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 biomarkers selected from tables 1, 2, 3 and 4.

In one embodiment, the kit for predicting the presence of reproductive cells in a testis of an infertile or hypofertile male subject may further comprise means for detecting in a seminal plasma sample of said subject at least one biomarker selected from the Table 5.

Typically, the kits may include binding partners as above described. For example, the kit may comprise a set of biomarkers antibodies as above defined, and that may be pre-labelled. Alternatively, probes may be unlabelled and the ingredients for labelling may be included in the kit in separate containers. The kit may further comprise hybridization reagents or other suitably packaged reagents and materials needed for the particular hybridization protocol, including solid-phase matrices, if applicable, and standards.

The invention will be further illustrated by the following figures and examples. However, these examples and figures should not be interpreted in any way as limiting the scope of the present invention.

FIGURES

FIG. 1:

Validation of predicted markers of the urogenital tract. A. Western blot analysis of TKTL1, LDHC and PGK2 in human tissues. Protein extracts (20 µg) from human testis (T); the head, body and tail of the epididymis (EpH, EpB and EpT, respectively), seminal vesicle (SV), prostate (P) and seminal plasma (SP) were separated on 12% polyacrylamide gels, electrotransferred onto PVDF membranes and probed with specific antibodies. TKTL1, LDHC and PGK2 were detected only in the testicular protein extract and in normal seminal plasma. B. Immunolocalization of TKTL1, LDHC, PGK2 along the male urogenital tract. Tissues were fixed by immersion in a formalin fixative and embedded in paraffin. Sections (5 µm) were dewaxed, rehydrated and incubated with antibodies against TKTL1, LDHC, PGK2. Complexes were revealed using a strepavidin-peroxidase amplification combination and sections were counterstained with Masson hematoxylin. TKTL1, LDHC and PGK2 immunoreactivities were detected only in the testis. TKTL1 immunostaining was present in all germ cells, with spermatogonia (arrowheads) exhibiting the strongest staining LDHC was detected in meiotic spermatocytes (arrowheads) and post-meiotic spermatids (arrows), and PGK2 was detected only in post-meiotic spermatids (arrows). Some residual immunostaining for PGK2 and to a lesser extent for LDHC was observed in epithelial cells in the epididymis head sections (arrowheads). Scale bars: 100 µm. C. Screening for the testicular germline markers TKTL1, LDHC and PGK2 in the seminal plasma of normal and infertile donors. Seminal plasmas (50 µg protein) from fertile donors (lanes 1-5 and 10-13), subjects with non-obstructive azoospermia (lanes 7, 8, 14, 15 and 18), obstructive azoospermia (lanes 9, 16) or postvasectomized men (lanes 6, 17) were separated on 12% polyacrylamide gels, electrotransferred onto PVDF membranes and probed with specific antibodies. TKTL1, LDHC and PGK2 proteins were all detected in seminal plasmas from fertile donors only.

EXAMPLES

Example 1

Materials and Methods:

The solid-phase combinatorial peptide Library-1 (ProteoMiner™) and carboxylated version (Library-2) were both from Bio-Rad Laboratories (Hercules, Calif., USA) as well as materials for electrophoresis such as plates and reagents. Sequencing grade trypsin was from Promega (Madison, Wis., USA). All other chemicals were from Sigma-Aldrich (Saint Quentin Fallavier, France).

Methods:

Human Seminal Plasma Collection

Proteomic analysis was conducted on pooled ejaculates from a single healthy donor which were processed as described elsewhere (13). Briefly, fresh ejaculates were recovered on ice and immediately centrifuged at 14000 g for 5 minutes at 4° C. The supernatants were supplemented with protease inhibitors (Complete™ Protease Inhibitor Cocktail; Roche Applied Science) prior to ultracentrifugation at 105000 g for 45 minutes at 4° C. For each ejaculate, the clear supernatant resulting from ultracentrifugation was stored at −80° C. until use. Protein concentration was finally determined in pooled ejaculates using the bicinchoninic acid (BCA) protein assay (Sigma-Aldrich).

For western blot analyses, seminal plasmas from subjects undergoing infertility check-up were collected following the current World Health Organization (WHO) guidelines. After liquefaction at room temperature for 30 minutes, seminal plasmas were centrifuged at 14000 g for 10 minutes at 4° C., complemented with anti-proteases (Complete™ Protease Inhibitor Cocktail; Roche Applied Science) and ultracentrifuged at 105000 g at 4° C. for 60 min. The protein concentration was then determined using the BCA protein assay (Sigma-Aldrich) prior storage at −80° C.

Combinatorial Peptide Ligand Library Fractionation of Seminal Plasma Proteins

The seminal plasma (472 mg proteins) was loaded onto a column (6.6 mm I.D.×32 mm in length) containing 1 ml of $NH_2$-Library (Fractions E) at a flow rate of 0.25 mL/min. The column effluent was continuously injected in a second column of the same dimensions packed with COOH-Library (Fractions S). The columns connected in series were then washed with a phosphate buffered saline (PBS) until UV baseline of the effluent of the second column was reached. After the wash, each individual column was subjected to four distinct elutions (Fractions 1 to 4) using respectively a 1M sodium chloride solution in water, a TUC solution (2 M thiourea, 7 M urea, 2% CHAPS), a UCA solution (9 M urea, citric acid up to pH 3.3) and a hydroorganic solution (HOS) composed of 6% v/v acetonitrile, 12% v/v isopropanol, 10% v/v of ammonia at 20% and 72% v/v water. When necessary, the eight eluates (Fractions E1 to E4, and S1 to S4) were immediately neutralized and submitted to protein content analysis using the Bradford-Lowry standard spectrophotometric method, desalted by dialysis at 4° C. against a 10 mM ammonium carbonate solution (cut off of dialysis membrane was 1000 Da) and then lyophilized.

Nano-LC-MS/MS Analysis of Human Seminal Plasma Proteins

Eluates from the Proteominer™ fractionation were resuspended in the adequate volume of 50 mM ammonium bicarbonate to adjust sample concentration at 1 mg/mL. Five μg proteins of each fraction were then reduced with 3 μL of a 65 mM DTT solution for 15 min (first incubation) at 37° C., and then alkylated with 3 μL of a 135 mM iodoacetamide solution (second incubation), in the dark at room temperature for 15 min. Digestion was carried out during 4 hours at 37° C. with 2 μL of 0.1 μg/μL modified trypsin (Promega, Madison, Wis., USA) in 50 mM ammonium bicarbonate.

The peptide mixtures were analyzed by nano-LC-MS/MS on a LTQ-Orbitrap XL mass spectrometer (Thermo Fisher Scientific, Bremen, Germany). 10 μL of each proteolytic digest (approximately 1 μg of proteins) were separated by reversed phase chromatography using a Accela MS pump (Thermo Fisher Scientific) with flow splitter delivering 300 nL/min post split. Samples were loaded onto a C18 trapping cartridge (CapTrap™; MICHROM Bioresources, Inc.) and separated onto a C18 (Reprosil) packed tip column (100 μm id×15 cm; Nikkyo Technos Co. Ltd). Peptides were eluted with 5 to 40% acetonitrile in 0.1% formic acid gradient of 120 min (including column equilibration). Full-scan mass spectra were acquired with the Orbitrap mass spectrometer at 60000 resolving power and the seven most intense peptides were automatically selected for CID MS/MS scans in parallel in the linear ion trap (LTQ). An ESI voltage of 2.2 kV was applied directly to the HPLC buffer using the liquid junction provided by the nanoelectrospray Ion Max source (Thermo Fisher Scientific). The ion transfer tube temperature was set to 200° C. Ion injection times were calculated for each spectrum to accumulate 1E6 ions in the Orbitrap for full MS scans and 10000 ions in the LTQ for MS/MS scans. Normalized collision energy was set to 35% with activation time of 30 ms. The MS/MS triggering threshold was set to 2000 counts to avoid triggering fragmentation too early during the peptide elution profile. Previously selected peptides were dynamically excluded for 120 s with a mass tolerance of +/−10 ppm. Repeat count was set to 1 and an exclusion list size of 500 was used. Singly charged precursors were rejected. The maximum injection time was set to 500 ms and 300 ms for full MS and MS/MS scan events respectively.

Data Processing and Analysis

The Proteome Discoverer software (version 1.2; Thermo Fisher Scientific) with the SEQUEST® search algorithm was used for protein identification. MS/MS spectra were searched against UniProt human Database (Release 15.3; Feb. 26, 2008; 356,194 sequences; 127,836,513 residues) for peptide characterisation and protein identification. The enzyme selectivity was set to full trypsin with one miss cleavage allowed. Modifications selected were set as fixed carbamidomethylation of cysteines, variable oxidation of methionine and variable deamidation of asparagine and glutamine. Identified peptides were filtered based on Xcorr values to obtain a false discovery rate of 1%. Proteome Discoverer software was used to generate lists of identified peptides in order to exclude them for subsequent LC-MS/MS analyses. Lists of not filtered out peptides were exported as a text file containing uncharged mass values with 5 decimals mass precision and a retention time window of +/−1 minute.

Accurate exclusion lists were then imported in the Xcalibur™ method file (Xcalibur Software version 2.0.7; Thermo Fisher Scientific). Other data dependent settings were crucial for the success of the strategy. The instrument configuration was set to work with uncharged masses and to automatically calculate the mass of a peptide based on its exact mass and charge state. A mass tolerance of ±10 ppm was used to reject previously identified peptides within the specified retention time window. Using lower values can result in the reselection of masses because, when using a parallel mode of operation on a LTQ Orbitrap XL, the parent ion selection for an ion trap MS/MS is based on an Orbitrap preview scan. This preview scan is acquired at a lower resolution (RP 15,000) than the final Orbitrap full scan, so the masses are less accurate.

A total of 3 acquisitions per sample were performed following this strategy. For the third analysis, results files from the first two runs were combined in Proteome Discoverer software to generate a second exclusion list that contained peptides identified from the first and second acquisitions. A second cycle of database search was then performed with SEQUEST® allowing for semi specificity of the trypsin enzyme. For these semi-trypsic analyses only a subset of UniProt human database was considered containing proteins identified from the full trypsin search and proteins identified in seminal plasma by three previous studies (13, 23-24).

Modifications selected were set as above. The list of identified proteins is provided in Supplemental Data 1.

Mapping of Protein IDs from Other Datasets

Protein identifiers from previous studies (GI numbers, (23); UniProt Entry names, (24); UniProt Accession numbers, (13), were retrieved and converted into current UniProt Accession numbers using the UniProt Batch retrieval and ID mapping modules (http://www.uniprot.org; release 15.3—May 26, 2009). All UniProt accession numbers were further linked to EntrezGene identifiers that were mapped to corresponding probesets on HG-U133 Plus 2.0 GeneChip® arrays using the Affymetrix CSV file (http://www.affymetrix.com/index.affx; version 28—Mar. 12, 2009) for tissue-profiling analysis. Retrieved UniProt IDs were used as non-redundant entries to compare the different dataset.

Microarray Tissue Profiling Experiments

Human Seminal Vesicles Dataset

Normal seminal vesicles were obtained at the Rennes University Hospital from subjects who underwent radical prostatectomy. The protocol was approved by the local ethics committee of Rennes, and informed consent was obtained from the donors. Total RNAs were extracted using Trizol reagent (Invitrogen, Cergy Pontoise, France), purified with phenol-chloroform, cleaned-up using RNeasy Total RNA Isolation Kit (Qiagen, Courtaboeuf, France), precipitated with ethanol and resuspended in RNAse-free water. Purified RNAs were then quantified with a NanoDrop ND-1000 (Thermo Fisher Scientific) and quality controlled on RNA Nano 6000 Chips and the Bioanalyser 2100 (Agilent, Santa Clara, Calif., USA). Total RNAs (500 ng) were used as templates in an in vitro transcription reaction using the GeneChip® 3' IVT Express Kit (Affymetrix, Santa Clara, Calif., USA) according to the manufacturer' instructions. Purified labeled cRNAs (20 µg) were fragmented and hybridized to HG-U133 Plus 2.0 GeneChip® arrays (Affymetrix). GeneChips were then washed using a GeneChip® Fluidics Station 450 (Affymetrix) and stained with streptavidin-phycoerythrin (SAPE) according to the manufacturer's instructions. Genechips® were finally scanned with a GeneChip® scanner 3000 7G (Affymetrix). Raw image files (DAT) as well as feature-level data files (CEL) were finally generated using the Affymetrix GeneChip® Command Console (AGCC) and are available on the NCBI Gene Expression Omnibus public repository (GSE17340).

Normalization and Filtration Procedures

CEL files corresponding to testicular samples (E-TABM-130; (26)) were downloaded from the NCBI GEO and from the EBI ArrayExpress (http://www.ebi.ac.uk/microarray-as/ae/) public repositories. They were further uploaded into the AMEN software (http://sourceforge.net/projects/amen/; (27)) and submitted to the RMA normalization procedure (28). Expression signals of sample replicates were then averaged and an empirical approach was used to identify transcripts detected in a single tissue only. To be considered as specifically expressed in a given tissue, signal intensities had to be above the median value (4.94531056811573) in that tissue and under this value in all other tissues. To avoid inclusion of expression signal close to this threshold, a fold change of ≥3 between the given sample and all other tissues was further required. Selected probesets were finally submitted to a last statistical filtration (Limma statistical test, FDR<1%; (29)) to remove those included because of aberrant replicate values. The list of selected probesets was then compared to that corresponding to proteins identified in the human seminal plasma.

Western Blot Analysis

Tissue samples (around 50 mg) were homogenized as previously described (30) using a TissueLyser (Qiagen) at 30 Hz for 2 minutes. After centrifugation (15,000×g, 1 h, 4° C.) proteins were quantified using the BCA protein assay (Sigma-Aldrich) and stored at −80° C. until use. Protein extracts (20 µg for tissues, 50 µg for seminal plasmas) were subjected to electrophoresis in 12% polyacrylamide gels and electrotransferred onto polyvinylidene difluoride (PVDF) Immobilon-PSQ membranes (Millipore, Saint-Quentin-en-Yvelines, France). After blocking nonspecific protein binding sites in Tris-buffered saline (TBS) containing 5% (w/v) non-fat dry milk and 0.1% Tween™ (nonionic detergent), the blots were incubated with primary antibodies in 0.1% Tween™ (nonionic detergent), 5% nonfat dry milk TBS. Blots were washed in TBS and then incubated with peroxidase conjugated secondary antibodies (GE Healthcare, Orsay, France; 1:10 000 in 5% non-fat dry milk TBS). Blots were washed again in TBS, and immunoreaction was detected with the enhanced chemiluminescence system ECL+ (GE Healthcare). The primary antibodies used were the mouse monoclonal anti-TKTL1 antibody (Ref WH0008277M1; Sigma-Aldrich) at a final dilution of 1/200, the rabbit monoclonal anti-LDHC (Ref ab52747; abcam, Paris, France) at a final dilution of 1/10000, and the rabbit polyclonal anti-PGK2 antibody (Ref AV53820; Sigma-Aldrich) at final dilution of 1/160. Western blots were carried out 3 times and representative signals are presented.

Immunohistochemistry

Immunohistochemical experiments were performed on Bouin-fixed and paraffin-embedded human tissues as previously described (30). Antibodies directed against TKTL1, LDHC, PGK2 were all used at a final dilution of 1/200.

Supplementary Information:

Results:

Fractionation of Human Seminal Plasma Using Combinatorial Peptide Ligand Libraries.

Proteomic studies of complex biological fluids, such as seminal plasma, are limited by the large dynamic range of protein species present in the fluid, which limits access to low-copy-number proteins. To overcome, or at least attenuate this limitation, the inventors used the Proteominer™ library technology to prefractionate the seminal plasma from a healthy donor prior to beginning proteome analysis. Non-liquefied seminal plasma was first loaded onto two different peptide libraries to concentrate the low-copy-number proteins. The retained proteins were then subjected to four different elutions, which generated eight subproteome fractions, each potentially enriched for proteins with different biochemical properties. These fractions, as well as the initial crude sample and the final flow through, were then trypsin-digested and injected into a LTQ-Orbitrap™ XL mass spectrometer to characterize the peptides by nano-LC-MS/MS analysis using the Proteome Discoverer software. The fractions exhibited very different patterns upon SDS-PAGE analysis.

Whereas 553 different peptides were successfully characterized in crude human seminal plasma, between 156 and 942 peptides were characterized for the Proteominer™ fractions which together led to a total of 2350 peptide characterizations. Interestingly, only, between 156 and 376 peptides were characterized in the S1 to S4 fractions, whereas between 434 and 942 peptides were characterized, which corresponded to 70% more peptides (in fraction E4) than the crude seminal plasma. A similar trend was observed for protein identification, as the number of unique species identified in the richest eluate (fraction E4; 242 unique proteins) was 92% higher than that in the crude biofluid (126 unique proteins).

The fractions exhibited very different patterns upon SDS-PAGE analysis (data not shown). The content of fractions indeed appeared heterogeneous in terms of complexity and elution from the second library notably appeared to contain less protein species. Importantly, these few proteins were different from those eluted from the first library (NH2-library; fractions E1-4), thus confirming the benefice of this second library (COOH-library; fractions S1-4) for capturing new protein species (21).

Overall, nano-LC-MS/MS analysis of the 8 Proteominer™ fractions together with the flowthrough led to a 4-fold increase in peptide characterisation (2435 non redundant peptides) and protein identification (488 unique proteins).

Nano-LC-MS/MS Analysis Using an Iterative Exclusion List Strategy

Whereas fractionation using peptide ligand libraries clearly improved the yield of proteins identified in human seminal plasma, the inventors also developed an exclusion list strategy for nano-LCMS/MS analysis with the aim of increasing peptide identification in Proteominer™ fractions. Following a first injection and identification step, fractions were injected a second time into the instrument and an Xcalibur™ method file was adjusted to focus on peptides that had not been characterized previously. This allowed us to characterize between 15% (Fraction S3) and 70% (Fraction E1) more peptides. This corresponded to increases in protein identification of between ~7.5% and 45.5%, respectively. Finally a third nano-LC-MS/MS analysis using an exclusion list that combined peptides characterized in the two first injections, allowed up to 39% additional peptides to be characterized (Fraction S1) and up to 29% more proteins to be identified (Fraction S1). Overall, 81 additional proteins were thus identified during the second nanoLC MS/MS analysis, while the third run finally allowed for identifying 49 extra proteins, bringing the total number of proteins identified in this study to 618.

The combination of Proteominer™ prefractionation on the two peptide libraries and our iterative exclusion list strategy appeared to be a robust and efficient way to optimize protein identification and led to a 5-fold increase in the number of identified proteins compared to a simple LC-MS/MS analysis of the raw seminal plasma.

Unraveling the Human Seminal Plasma Proteome

Several attempts have been made to reveal the human seminal plasma proteome. Two systematic studies of normal human seminal plasma identified 916 (13) and 46 (23) proteins, respectively. Additionally, one study of the human prostasome proteome identified 136 proteins (24). Prior to concatenating these datasets to ours, protein identifiers from each dataset were retrieved and converted into UniProt accession numbers. This step was mandatory to manage redundancy and revealed that, overall, 1,126 unique proteins have been described so far in the human seminal plasma. The entire dataset appeared to be enriched in GO terms that are consistent with what we know or could expect from this biological fluid. Indeed, the most enriched annotations were linked to 'extracellular space' or 'secretory granules' (cellular component), involved gene products that bear 'exo-' or 'endopeptidase activities' (molecular function) or were proteins important for 'proteolysis' or 'protein folding' (biological process). The detailed description of the enriched and depleted GO terms annotation is given.

The different datasets, however, did not overlap completely as shown by a comparison between the three studies. In fact, only 55 identified proteins were common to all three studies, whereas 645 and 410 proteins were found in one and two studies, respectively. The different technological approaches employed in these studies may account for the low level of overlap among the sets of identified proteins. An additional explanation is that the higher molecular weight proteins, from which more tryptic peptides can be theoretically generated, are more likely to be identified by MS/MS. However the inventors found no such bias that was significantly linked to the size of the commonly identified proteins. A more likely explanation is that differences in the relative abundance of the proteins within the respective samples impacted the heterogeneity of the three datasets. Indeed, when using the number of characterized peptides as a reflection of protein abundance, the inventors showed that proteins found in multiple studies had been identified through a much higher number of peptides than those identified in only a single study. This clearly suggests that highly abundant proteins are those retrieved in most studies.

Identification of Biological Markers of the Human Male Reproductive Tract

Biological fluids represent a major potential source of markers, which may be used to detect pathological conditions in the organ(s) involved in their secretion. In humans, the seminal plasma is mainly composed of secretions from four organs: the seminal vesicles, the prostate gland, the epididymides and the testes, and it is likely to contain proteins specific to each of these organs. To test this hypothesis, the inventors performed a tissue-profiling analysis based on gene expression datasets for testis (initially produced by our laboratory). Using the median signal intensity as the expression cutoff—a commonly accepted estimation of the background in microarray experiments—and a change in expression of at least three-fold, the inventors first identified genes specifically expressed, or at least detected only in the testis (1,942 genes). The relevance of these genes to the biology of the testis was again confirmed by highlighting enriched GO terms related to either 'spermatogenesis' or 'meiosis' for the testis.

The inventors then focused on subsets of genes that were expressed in a tissue-specific manner and for which the corresponding gene product had also been identified in human seminal plasma. The inventors thus highlighted 77 testis proteins that represent potential markers in human seminal plasma. Importantly, most of the corresponding testis-specific genes were detected at high levels in the transcriptome datasets from isolated spermatocytes and spermatids, which made the corresponding proteins potential germline markers in human seminal plasma.

Validation of New Markers of Male Genital Tract Organs

In order to validate the biomarker status of some of the newly discovered proteins, the inventors performed western blot analyses and/or immunohistochemistry using commercially available antibodies directed against the selected proteins. TKTL1, LDHC and PGK2 were consistently detected in testicular extracts and seminal plasma only (FIG. 1A). Immunohistochemical studies further confirmed the testis-specific expression of TKTL1, LDHC and PGK2. TKTL1 was found expressed throughout germ cell development, with spermatogonia exhibiting the strongest labeling. LDHC was expressed in both meiotic spermatocytes and post-meiotic spermatids, whereas PGK2 was specifically observed in elongated spermatids (FIG. 1B). In the head segment of the epididymis, PGK2 and to a lesser extent LDHC immunoreactivities were present in epithelial cells (FIG. 1B). Conversely, LDHC and PGK2 gene expression was not detected in the epididymis, thus indicating protein reabsorption by this epithelium.

Finally, the inventors assessed the presence of potential testicular germline markers in the seminal plasma using sperm samples from fertile donors and from subjects exhibiting various anomalies/pathologies (FIG. 1C). Whereas TKTL1, LDHC and PGK2 were consistently detected in normal seminal plasmas, these proteins were either undetectable or barely detectable in seminal plasmas from subjects with NOA, OA and post-vasectomized men (FIG. 1C). Conversely, proteins specific to other organs of the reproductive tract were detected at similar levels in the different seminal plasmas.

Discussion

Deciphering the seminal plasma proteome is important for gaining new insights into the physiopathology of spermatogenesis. Numerous attempts were made over the past decade to unravel the seminal plasma content. The success of these efforts improved over time as the resolution and power of the available technologies improved (for example see (13, 23, 24 and 31)). Our study provides the most in-depth proteomic analysis to date of the human seminal plasma. With the goal of constructing a comprehensive annotation of this proteome, the inventors identified a total of over 1,100 gene products either directly or by inference from previously published work. The inventors also designed a "combinatorial omics" approach to integrate the proteomic data with the transcriptomic profiles of the organs that produce this biofluid. Using this innovative method, the inventors identified multiple potential organ marker proteins that could be used to create molecular signatures of normal seminal plasma and that produced by men with reproductive disorders. In particular, the inventors identified testicular germline biomarkers whose presence or absence in seminal plasma could be used by clinicians as a diagnostic decision tool for the management of male infertility.

In this study, the inventors focused first on the proteomic analysis of human seminal plasma. The inventors combined sample pre-fractionation using peptide ligand library columns with subsequent shotgun nano-LC-MS/MS analysis of the tryptic peptides corresponding to each elution fraction. Ligand libraries have been shown to be a key technology for capturing low-abundance proteins of the so-called "deep" proteome in biological fluids (18-20). Although the success of decreasing the dynamic range of protein concentrations with the Proteominer™ library is difficult to evaluate in the present study, the sequential elution of proteins bound to the library columns clearly produced enriched fractions that allowed higher numbers of proteins to be identified.

Additionally, it was important to optimize the number of proteins in the injected samples that could be identified by mass spectrometry. When using LC-MS/MS to perform shotgun proteomics studies, standard data-dependent acquisition (DDA) inherently limits the capacity of these instruments to completely analyze complex mixtures (32-33). Indeed, DDA methods sample the most intense precursor ions while concurrently failing to sequence those lower intensity ions generated by less abundant proteins (34). This is why the inventors tested a new nano-LCMS/MS strategy to investigate the poorly represented species in each elution fraction. This involved re-injecting the sample for a second analysis by LC-MS/MS in which the previously identified peptides were excluded. Such an approach to performing a thorough sampling of complex protein mixtures was first described by Rudomin et al. (35) and is based on the use of accurate mass exclusion-based DDA (AMEx). In our hands, this procedure was performed twice for a total of three LC-MS/MS acquisitions per sample. Database search results were combined to determine the total number of peptides and proteins identified in each sample and in the entire analysis. Compared to most on-the-fly strategies, the workflow we describe here allowed us to focus on low-intensity peptides, which resulted in the identification of more than 50% additional proteins in some individual fractions. This straightforward and easy-to-automate procedure therefore represents a promising alternative for obtaining the most information from precious samples. This strategy appeared to be more efficient than repeated identical standard DDA runs and is more effective than the known inclusion list-based approach (36-37) because it improves the detection of unique peptides as early as the second injection, after the first exclusion list is applied. It also allowed us to reinforce identification of 82 proteins initially identified through a single peptide characterization.

One of the pitfalls of studying seminal plasma is that upon ejaculation, the fluid coagulates mainly due to the presence of semenogelins. The sperm liquefaction that takes place shortly thereafter corresponds to the known physiological cleavage of these proteins by the combined action of PSA (prostatic-specific antigen) and PAP (prostatic acid phosphatase). This leads to the formation of a number of semenogelin cleavage peptides with various activities (38). PSA and PAP may also act on numerous other seminal plasma proteins to produce a large array of peptides that cannot be predicted from classical trypsin digestion patterns. The inventors then decided to perform a semi-tryptic analysis to facilitate the identification of such peptides and to improve our protein identification yield. Overall, this semi-tryptic analysis allowed us to identify 38 additional proteins.

After our analysis of the human seminal plasma proteome was completed, the list of identified proteins was merged with existing datasets obtained published studies. This led to a total dataset of over 1,100 non-redundant proteins. The following step was then to develop a "combinatorial omics" approach that relied on extracting meaningful information from the lists of proteins identified from our proteomics analysis by using transcriptome gene expression data for the testis involved in a biofluid production. Our idea was to demonstrate that it is possible to highlight proteins of interest without performing the so-called "differential studies" generally employed to compare normal and pathological biofluids. Our total protein dataset was then used as a reference for the normal seminal plasma proteome and expression of the corresponding genes was investigated using Affymetrix gene expression microarray datasets for the testis involved in seminal plasma production. Through this analysis, the inventors identified numerous proteins specific to each of these organs and, notably, found 40 seminal plasma proteins for which expression of the corresponding genes was detected in the testis only. Importantly, most of these genes were specifically expressed in germ cells, as evidenced by the high levels of these proteins found in isolated spermatocyte and spermatid extracts. When investigated by immunohistochemistry, some genes appeared to be expressed throughout the different germ cells (i.e, TKTL1) whereas others were restricted to meiotic and/or post-meiotic germ cells (i.e, LDHC and PGK2).

Sperm recovery attempts are often unsuccessful for NOA subjects and markers that would predict sperm-positive testicular biopsies are absolutely required for clinicians to improve subjects counseling and to reduce both the financial and psychological costs of such procedures. Several indicators have been proposed to be potential indirect markers for the presence of spermatozoa in the testis. These include examination parameters (i.e. 2D:4D finger length ratio) and factors secreted by Sertoli cells (e.g. inhibin A and B, AMH). The low levels of inhibin A in the blood however prevent it from being routinely measurable (39-41), and whether the level of inhibin B, either in seminal plasma or in the blood, correlates with the presence of testicular spermatozoa in NOA subjects is controversial (42-46). Although one study reported that AMH levels were lower in subjects with NOA compared to subjects with obstructive azoospermia (47), the potential of AMH as a marker of positive biopsy for sperm recovery has not been further evaluated.

Thus, a combination of the specific germ cell protein markers identified in our study, such as TKTL1, LDHC and PGK2, might be used to develop a seminal plasma assay and diagnose NOA subjects so that only subjects for whom the probability of finding live spermatozoa is high are selected for TESE. A Sertoli-Cell-Only syndrome would thus be negative for all three markers. Subjects with maturation arrests at either the spermatogonia or spermatocyte stages would likely be positive for either TKTL1 or TKTL1 and LDHC, respectively. Finally, subjects with complete spermatogenesis would be positive for TKTL1, LDHC and PGK2. However, detecting germ cell markers in the seminal plasma may be impractical routinely. Indeed, in some pathological NOA situations only a few nests of residual spermatogenesis can be present in various areas of the testes. As a consequence the expected germ cell protein markers could be found at very low amounts in the seminal plasma. Using western blots, the inventors successfully detected germ cell markers in normal seminal plasma, and thus were able to distinguish it from seminal plasma with no spermatozoa. The many constraints of western blots make it a cumbersome method for routinely identifying NOA subjects likely to yield a positive biopsy. For this reason, the inventors develop a diagnostic multiplex antibody assay (Fertichip) for measuring the identified germ cell markers in seminal plasma. Monoclonal antibodies are produced for each of the individual reproductive cell biomarkers identified so far. The sensitivity and specificity of the assay is evaluated using large cohorts of seminal plasma from subjects with different fertility anomalies and pathologies.

Recently, the seminal plasma proteome of fertile donors was compared to that of men who had undergone vasectomies (51). In this study, the proteins specific to the seminal plasmas of fertile donors were assumed to originate from the testis and/or the epididymis. This was partially confirmed by database searching and literature mining. According to our tissue profiling experiment, the genes corresponding to 15 of the 32 potential protein markers identified by Batruch et al. were indeed found to be expressed only in either or both of these organs. However, the remaining ones appeared to be also expressed in other tissues, including the seminal vesicles and/or the prostate. This clearly illustrates that the lack of a protein being identified in a biofluid is not always a convincing indication that the protein is not present, and that targeted studies must continue so that candidate biomarkers can be validated. Despite this weakness, Batruch and collaborators identified more than 2,000 proteins to produce the largest protein dataset of human seminal plasma yet available. The inventors aim to integrate this dataset to gain new insights into gamete physiology and to identify more precise markers of the male urogenital tract. However, it will be important to describe proteins whose amounts in the seminal plasma are measurable with routine assays. This is likely to be a major challenge and may limit the numbers or utility of potential post-meiotic germ cell markers.

In the present invention, the inventors used a "combinatorial omics" approach involving in-depth proteomic characterization and bioinformatic mining of the human seminal plasma together with transcriptomic analysis to identify testis biomarkers involved in seminal plasma production. This concept study led to the identification of several specific protein biomarkers of post-meiotic germ cells whose presence might be monitored in seminal plasma by clinicians to better select only those NOA subjects for which a testis biopsy will have a high probability of yielding live spermatozoa. The inventors also demonstrated that "combinatorial omics" is a powerful strategy for identifying relevant biological markers in complex biofluids without the need for heavy proteomics approaches that rely on differential expression.

Example 2

The inventors have conducted studies to validate the relevance of the method according to the invention for predicting the presence of reproductive cells in the testis.

The inventors assessed the presence of two additional potential germline markers in the seminal plasma using sperm samples from fertile donors and from subjects exhibiting anomalies/pathologies. OTUB1 and SPACA3 were consistently detected in normal seminal plasmas, but were undetectable or barely detectable in seminal plasmas from subjects with NOA, OA and post-vasectomized men.

REFERENCES

Throughout this application, various references describe the state-of-the-art to which this invention pertains. The disclosures of these references are hereby incorporated by reference into the present disclosure.

1. Bruckert, E. (1991) How frequent is unintentional childlessness in Germany? *Andrologia* 23, 245-250.
2. Juul, S., Karmaus, W., and Olsen, J. (1999) Regional differences in waiting time to pregnancy: pregnancy-based surveys from Denmark, France, Germany, Italy and Sweden. The European Infertility and Subfecundity Study Group. *Hum Reprod* 14, 1250-1254.
3. Organization, W. H. (2000) Manual fot the standardized investigation, diagnosis and management of the infertile male. *In: Rowe P J, Comhaire F H, Hargreave T B and Mahmoud A M A, Eds* Cambridge University Press, Cambridge, pp. 5-11.
4. Palermo, G., Joris, H., Devroey, P., and Van Steirteghem, A. C. (1992) Pregnancies after intracytoplasmic injection of single spermatozoon into an oocyte. *Lancet* 340, 17-18.
5. Tournaye, H., Devroey, P., Liu, J., Nagy, Z., Lissens, W., and Van Steirteghem, A. (1994) Microsurgical epididymal sperm aspiration and intracytoplasmic sperm injection: a new effective approach to infertility as a result of congenital bilateral absence of the vas deferens. *Fertil Steril* 61, 1045-1051.
6. Craft, I., Bennett, V., and Nicholson, N. (1993) Fertilising ability of testicular spermatozoa. *Lancet* 342, 864.
7. Schoysman, R., Vanderzwalmen, P., Nijs, M., Segal, L., Segal-Bertin, G., Geerts, L., van Roosendaal, E., and Schoysman, D. (1993) Pregnancy after fertilisation with human testicular spermatozoa. *Lancet* 342, 1237.
8. Friedler, S., Raziel, A., Strassburger, D., Schachter, M., Bern, O., Kasterstein, E., Komarovsky, D., and Ron-El, R. (2008) The management of azoospermia. *In: Infertility and assisted reproduction* Chapter 52, pp. 478-492.
9. Silber, S. J., van Steirteghem, A., Nagy, Z., Liu, J., Tournaye, H., and Devroey, P. (1996) Normal pregnancies resulting from testicular sperm extraction and intracytoplasmic sperm injection for azoospermia due to maturation arrest. *Fertil Steril* 66, 110-117.
10. Carpi, A., Sabanegh, E., and Mechanick, J. (2009) Controversies in the management of nonobstructive azoospermia. *Fertil Steril* 91, 963-970.

11. Tournaye, H., Verheyen, G., Nagy, P., Ubaldi, F., Goossens, A., Silber, S., Van Steirteghem, A. C., and Devroey, P. (1997) Are there any predictive factors for successful testicular sperm recovery in azoospermic patients? *Hum Reprod* 12, 80-86.
12. Calvel, P., Rolland, A. D., Jegou, B., and Pineau, C. (2010) Testicular postgenomics: targeting the regulation of spermatogenesis. *Philos Trans R Soc Lond B Biol Sci* 365, 1481-1500.
13. Pilch, B., and Mann, M. (2006) Large-scale and high-confidence proteomic analysis of human seminal plasma. *Genome Biol* 7, R40.
14. Guerrier, L., Thulasiraman, V., Castagna, A., Fortis, F., Lin, S., Lomas, L., Righetti, P. G., and Boschetti, E. (2006) Reducing protein concentration range of biological samples using solid phase ligand libraries. *J Chromatogr B Analyt Technol Biomed Life Sci* 833, 33-40.
15. Righetti, P. G., Boschetti, E., Lomas, L., and Citterio, A. (2006) Protein Equalizer Technology: the quest for a "democratic proteome". *Proteomics* 6, 3980-3992.
16. Righetti, P. G., and Boschetti, E. (2008) The ProteoMiner and the FortyNiners: searching for gold nuggets in the proteomic arena. *Mass Spectrom Rev* 27, 596-608.
17. Boschetti, E., and Righetti, P. G. (2009) The art of observing rare protein species in proteomes with peptide ligand libraries. *Proteomics* 9, 1492-1510.
18. Castagna, A., Cecconi, D., Sennels, L., Rappsilber, J., Guerrier, L., Fortis, F., Boschetti, E., Lomas, L., and Righetti, P. G. (2005) Exploring the hidden human urinary proteome via ligand library beads. *J Proteome Res* 4, 1917-1930.
19. Sennels, L., Salek, M., Lomas, L., Boschetti, E., Righetti, P. G., and Rappsilber, J. (2007) Proteomic analysis of human blood serum using peptide library beads. *J Proteome Res* 6, 4055-4062.
20. Mouton-Barbosa, E., Roux-Dalvai, F., Bouyssie, D., Berger, F., Schmidt, E., Righetti, P. G., Guerrier, L., Boschetti, E., Burlet-Schiltz, O., Monsarrat, B., and de Peredo, A. G. (2010) Indepth exploration of cerebrospinal fluid by combining peptide ligand library treatment and label free protein quantification. *Mol Cell Proteomics* 9, 1006-1021.
21. Guerrier, L., Claverol, S., Fortis, F., Rinalducci, S., Timperio, A. M., Antonioli, P., Jandrot-Perrus, M., Boschetti, E., and Righetti, P. G. (2007) Exploring the platelet proteome via combinatorial, hexapeptide ligand libraries. *J Proteome Res* 6, 4290-4303.
22. Roux-Dalvai, F., Gonzalez de Peredo, A., Simo, C., Guerrier, L., Bouyssie, D., Zanella, A., Citterio, A., Burlet-Schiltz, O., Boschetti, E., Righetti, P. G., and Monsarrat, B. (2008) Extensive analysis of the cytoplasmic proteome of human erythrocytes using the peptide ligand library technology and advanced mass spectrometry. *Mol Cell Proteomics* 7, 2254-2269.
23. Fung, K. Y., Glode, L. M., Green, S., and Duncan, M. W. (2004) A comprehensive characterization of the peptide and protein constituents of human seminal fluid. *Prostate* 61, 171-181.
24. Utleg, A. G., Yi, E. C., Xie, T., Shannon, P., White, J. T., Goodlett, D. R., Hood, L., and Lin, B. (2003) Proteomic analysis of human prostasomes. *Prostate* 56, 150-161.
26. Chalmel, F., Rolland, A. D., Niederhauser-Wiederkehr, C., Chung, S. S., Demougin, P., Gattiker, A., Moore, J., Patard, J. J., Wolgemuth, D. J., Jegou, B., and Primig, M. (2007) The conserved transcriptome in human and rodent male gametogenesis. *Proc Natl Acad Sci USA* 104, 8346-8351.
27. Chalmel, F., and Primig, M. (2008) The Annotation, Mapping, Expression and Network (AMEN) suite of tools for molecular systems biology. *BMC Bioinformatics* 9, 86.
28. Irizarry, R. A., Hobbs, B., Collin, F., Beazer-Barclay, Y. D., Antonellis, K. J., Scherf, U., and Speed, T. P. (2003) Exploration, normalization, and summaries of high density oligonucleotide array probe level data. *Biostatistics* 4, 249-264.
29. Wettenhall, J. M., and Smyth, G. K. (2004) limmaGUI: a graphical user interface for linear modeling of microarray data. *Bioinformatics* 20, 3705-3706.
30. Com, E., Rolland, A. D., Guerrois, M., Aubry, F., Jegou, B., Vallet-Erdtmann, V., and Pineau, C. (2006) Identification, molecular cloning, and cellular distribution of the rat homolog of minichromosome maintenance protein 7 (MCM7) in the rat testis. *Mol Reprod Dev* 73, 866-877.
31. Starita-Geribaldi, M., Roux, F., Garin, J., Chevallier, D., Fenichel, P., and Pointis, G. (2003) Development of narrow immobilized pH gradients covering one pH unit for human seminal plasma proteomic analysis. *Proteomics* 3, 1611-1619.
32. Florens, L., Washburn, M. P., Raine, J. D., Anthony, R. M., Grainger, M., Haynes, J. D., Moch, J. K., Muster, N., Sacci, J. B., Tabb, D. L., Witney, A. A., Wolters, D., Wu, Y., Gardner, M. J., Holder, A. A., Sinden, R. E., Yates, J. R., and Carucci, D. J. (2002) A proteomic view of the *Plasmodium falciparum* life cycle. *Nature* 419, 520-526.
33. Durr, E., Yu, J., Krasinska, K. M., Carver, L. A., Yates, J. R., Testa, J. E., Oh, P., and Schnitzer, J. E. (2004) Direct proteomic mapping of the lung microvascular endothelial cell surface in vivo and in cell culture. *Nat Biotechnol* 22, 985-992.
34. Liu, H., Sadygov, R. G., and Yates, J. R., 3rd (2004) A model for random sampling and estimation of relative protein abundance in shotgun proteomics. *Anal Chem* 76, 4193-4201.
35. Rudomin, E. L., Carr, S. A., and Jaffe, J. D. (2009) Directed sample interrogation utilizing an accurate mass exclusion-based data-dependent acquisition strategy (AMEx). *J Proteome Res* 8, 3154-3160.
36. Piening, B. D., Wang, P., Bangur, C. S., Whiteaker, J., Zhang, H., Feng, L. C., Keane, J. F., Eng, J. K., Tang, H., Prakash, A., McIntosh, M. W., and Paulovich, A. (2006) Quality reference value metrics for LC-MS feature detection tools demonstrated on *Saccharomyces cerevisiae* proteomic profiles. *J Proteome Res* 5, 1527-1534.
37. Schmidt, A., Gehlenborg, N., Bodenmiller, B., Mueller, L. N., Campbell, D., Mueller, M., Aebersold, R., and Domon, B. (2008) An integrated, directed mass spectrometric approach for in-depth characterization of complex peptide mixtures. *Mol Cell Proteomics* 7, 2138-2150.
38. Lilja, H., Oldbring, J., Rannevik, G., and Laurell, C. B. (1987) Seminal vesicle-secreted proteins and their reactions during gelation and liquefaction of human semen. *J Clin Invest* 80, 281-285.
39. Illingworth, P. J., Groome, N. P., Byrd, W., Rainey, W. E., McNeilly, A. S., Mather, J. P., and Bremner, W. J. (1996) Inhibin-B: a likely candidate for the physiologically important form of inhibin in men. *J Clin Endocrinol Metab* 81, 1321-1325.
40. Anawalt, B. D., Bebb, R. A., Matsumoto, A. M., Groome, N. P., Illingworth, P. J., McNeilly, A. S., and Bremner, W. J. (1996) Serum inhibin B levels reflect Sertoli cell function in normal men and men with testicular dysfunction. *J Clin Endocrinol Metab* 81, 3341-3345.

41. Anderson, R. A., Irvine, D. S., Balfour, C., Groome, N. P., and Riley, S. C. (1998) Inhibin B in seminal plasma: testicular origin and relationship to spermatogenesis. *Hum Reprod* 13, 920-926.
42. Von Eckardstein, S., Simoni, M., Bergmann, M., Weinbauer, G. F., Gassner, P., Schepers, A. G., and Nieschlag, E. (1999) Serum inhibin B in combination with serum folliclestimulating hormone (FSH) is a more sensitive marker than serum FSH alone for impaired spermatogenesis in men, but cannot predict the presence of sperm in testicular tissue samples. *J Clin Endocrinol Metab* 84, 2496-2501.
43. Brugo-Olmedo, S., De Vincentiis, S., Calamera, J. C., Urrutia, F., Nodar, F., and Acosta, A. A. (2001) Serum inhibin B may be a reliable marker of the presence of testicular spermatozoa in patients with nonobstructive azoospermia. *Fertil Steril* 76, 1124-1129.
44. Vernaeve, V., Tournaye, H., Schiettecatte, J., Verheyen, G., Van Steirteghem, A., and Devroey, P. (2002) Serum inhibin B cannot predict testicular sperm retrieval in patients with nonobstructive azoospermia. *Hum Reprod* 17, 971-976.
45. Guthauser, B., Bailly, M., Bergere, M., Wainer, R., Ville, Y., and Selva, J. (2002) Successful pregnancy and delivery after testicular sperm extraction despite an undetectable concentration of serum inhibin B in a patient with nonobstructive azoospermia. *Fertil Steril* 77, 1077-1078.
46. El Garem, Y. F., El Arini, A. F., El Beheiry, A. H., Zeid, S. A., and Comhaire, F. H. (2002) Possible relationship between seminal plasma inhibin B and spermatogenesis in patients with azoospermia. *J Androl* 23, 825-829.
47. Fenichel, P., Rey, R., Poggioli, S., Donzeau, M., Chevallier, D., and Pointis, G. (1999) Anti-Mullerian hormone as a seminal marker for spermatogenesis in non-obstructive azoospermia. *Hum Reprod* 14, 2020-2024.
51. Batruch, I., Lecker, I., Kagedan, D., Smith, C. R., Mullen, B. J., Grober, E., Lo, K. C., Diamandis, E. P., and Jarvi, K. A. (2011) Proteomic Analysis of Seminal Plasma from Normal Volunteers and Post-Vasectomy Patients Identifies over 2000 Proteins and Candidate Biomarkers of the Urogenital System. *J Proteome Res* 10, 941-953.
52. Sato T, Katagiri K, Gohbara A, Inoue K, Ogonuki N, Ogura A, Kubota Y, Ogawa T. In vitro production of functional sperm in cultured neonatal mouse testes. Nature. 2011; 471(7339):504-7.
53. Sato T, Katagiri K, Yokonishi T, Kubota Y, Inoue K, Ogonuki N, Matoba S, Ogura A, Ogawa T. In vitro production of fertile sperm from murine spermatogonial stem cell lines. Nat Commun. 2011; 2:472. doi: 10.1038/ncomms1478.
54. Lemoine J, Fortin T, Salvador A, Jaffuel A, Charrier J P, Choquet-Kastylevsky G. The current status of clinical proteomics and the use of MRM and MRM(3) for biomarker validation. Expert Rev Mol Diagn. 2012 May; 12(4):333-42.

The invention claimed is:

1. A method for recovering reproductive cells in the testis of an infertile or hypofertile male subject afflicted with non-obstructive azoospermia, comprising the steps of
    measuring in a seminal plasma sample obtained from said subject an expression level of at least one biomarker expressed in said reproductive cells selected from the group consisting of CELSR1, CT47A1-9, ART3, MAPK1, ARHGAP9, PTPN21, ZNF569, TFRC, TMED4, MLLT4, MKI67, HIST1H2BJ, DSG1, FGG, HIST1H2BA, GART, MCM3AP, PITHD1, AMBP, SI, SLC44A5, GNAO1, GNAS, ANXA2, INPP4B, SLC7A2, APOA2, EEF1E1, MAP6, RAB27B, ABCB11, SEMA3D, ATP1B3, DNASE1, TOLLIP, BROX, AHCYL2, PSMD6, TPPP2, PRDD54, AQP5, PRKACG, XPNPEP1, GALC, FAM35B, ACE, DDX3X, EIF4A2, PRND, PGLYRP2, TUBB4, INHA, ACE2, APOA1, ZDHHC20, TEX101, DPEP3, PRPS1L1, ZPBP, ZPBP2, ADAM32, TEKT3, GAPDHS, TRIM36, TKTL2, SPAM1, LYZL2, SPACA3, OTUB2, AKAP4, RFFL, and GLYPR1L1;
    comparing the expression level of the at least one biomarker detected in the seminal plasma sample with a reference value;
    determining the presence of reproductive cells in the testis of the subject wherein a higher expression level of the at least one biomarker in the sample relative to an infertile control subject and/or an equivalent or higher expression level of the at least one biomarker in the sample relative to a fertile control subject is indicative of a high probability of reproductive cells being present in the testis of the subject; and
    recovering said reproductive cells from the testis of the infertile or hypofertile male subject afflicted with non-obstructive azoospermia if the reproductive cells are determined to be present in the testis of said subject.

2. The method according to claim 1 which further comprises a step of measuring an expression level of at least one biomarker selected from the group consisting of TKTL1, LDHC, PGK2, AHSG, and PGAM2.

3. The method of claim 1, wherein the expression level of at least two biomarkers are measured.

4. The method of claim 1, wherein the expression level of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 biomarkers are measured.

5. The method of claim 1, wherein said reproductive cells are recovered via a biopsy.

6. The method of claim 5, wherein said biopsy is testicular sperm extraction (TESE).

7. The method of claim 1, wherein said step of measuring includes the detection of a labeled probe complexed with said at least one biomarker.

* * * * *